United States Patent
Evans et al.

(10) Patent No.: US 8,889,593 B2
(45) Date of Patent: Nov. 18, 2014

(54) HERBICIDAL COMPOSITIONS BASED ON 3-PHENYLURACILS AND 3-SULFONYLISOXAZOLINES

(75) Inventors: Richard R. Evans, Greenville, MS (US); Rex Liebl, Raleigh, NC (US); Robert Reinhard, Ludwigshafen (DE); Helmut Walter, Obrigheim (DE); Cyrill Zagar, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1444 days.

(21) Appl. No.: 11/908,635

(22) PCT Filed: Mar. 16, 2006

(86) PCT No.: PCT/EP2006/060792
§ 371 (c)(1),
(2), (4) Date: Sep. 14, 2007

(87) PCT Pub. No.: WO2006/097509
PCT Pub. Date: Sep. 21, 2006

(65) Prior Publication Data
US 2009/0042727 A1    Feb. 12, 2009

Related U.S. Application Data

(60) Provisional application No. 60/662,362, filed on Mar. 17, 2005.

(51) Int. Cl.
*A01N 43/54*    (2006.01)
*A01N 43/80*    (2006.01)
*A01N 43/02*    (2006.01)
*A01N 43/36*    (2006.01)

(52) U.S. Cl.
CPC ............... *A01N 43/54* (2013.01); *A01N 43/80* (2013.01)
USPC ............ 504/136; 504/138; 504/140; 514/256

(58) Field of Classification Search
USPC ............................ 504/136, 138, 140; 514/256
See application file for complete search history.

(56) References Cited

U.S. PATENT DOCUMENTS

| | | | |
|---|---|---|---|
| 6,841,519 B1 | 1/2005 | Nakatani et al. | |
| 7,238,689 B2 | 7/2007 | Nakatani et al. | |
| 2004/0259734 A1 | 12/2004 | Nakatani et al. | |
| 2005/0215797 A1 | 9/2005 | Nakatani et al. | |
| 2005/0256004 A1 | 11/2005 | Takahashi et al. | |

FOREIGN PATENT DOCUMENTS

| | | | |
|---|---|---|---|
| JP | 09/328483 A | 6/1996 | |
| JP | 2004/002324 A | 3/2002 | |
| JP | 2005/035924 A | 7/2003 | |
| JP | 2004 002324 A | 1/2004 | |
| WO | WO 01/83459 A2 | 11/2001 | |
| WO | WO 01/83459 A3 | 11/2001 | |
| WO | WO 03/010165 A1 | 2/2003 | |
| WO | WO 03/024221 A | 3/2003 | |
| WO | WO 03/024221 A1 | 3/2003 | |
| WO | WO 2004/014138 A | 2/2004 | |
| WO | WO 2004/080183 A | 9/2004 | |
| WO | WO 2004/080183 A1 | 9/2004 | |

OTHER PUBLICATIONS

Farm Chemical Handbook 2000, vol. 86, Meister Publishing Co., 2000, Table of Contents (3 pgs).
B. Hock et al., Stuttgart 1995, "Herbizide", pp. 1-8.
W. H. Aherns, Herbicide Handbook, $7_{th}$ Edition, Weed Science Society of America, 1994, Table of Contents (4 pgs.).
K. K. Hatzios, Herbicide Handbook, Supplement to $7_{th}$ Edition, Weed Science Society of America 1998, Table of Contents (4 pgs.).
S. R. Colby (1967), "Calculating synergistic and antagonistic responses of herbicide combinations", Weeds 15, pp. 20-22.

*Primary Examiner* — Abigail Fisher
*Assistant Examiner* — Andriae M Holt
(74) *Attorney, Agent, or Firm* — Rothwell, Figg, Ernst & Manbeck, P.C.

(57) ABSTRACT

A herbicidal composition comprising
a) at least one 3-phenyluracils of formula I

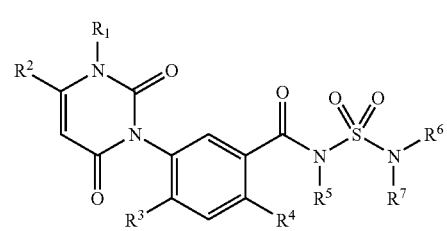

wherein the variables $R^1$ to $R^7$ are as defined in the specification; and
b) at least one 3-sulfonylisoxazoline of formula II

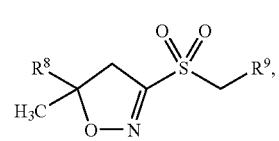

wherein the variables $R^8$ and $R^9$ are as defined in the specification; and
c) optionally at least one safener III selected from the group as defined in the specification.

18 Claims, 1 Drawing Sheet

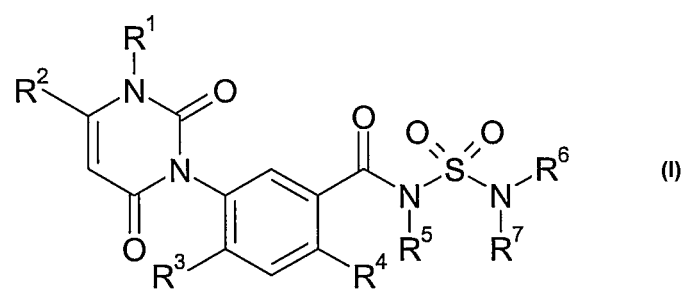
(I)
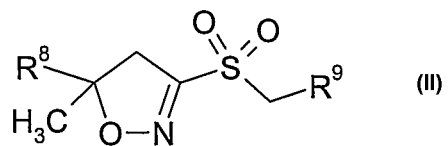
(II)

HERBICIDAL COMPOSITIONS BASED ON 3-PHENYLURACILS AND 3-SULFONYLISOXAZOLINES

CROSS REFERENCE TO RELATED APPLICATION

This application is a 35 USC §371 National Phase Entry Application from PCT/EP2006/060792, filed Mar. 16, 2006, and designating the United States, which claims the benefit of U.S. Provisional 60/662,362, filed Mar. 17, 2005.

The present invention relates to herbicidally active compositions comprising 3-phenyluracils of formula I, 3-sulfonylisoxazolines of formula II and optionally at least one safener of formula III.

In crop protection products, it is desirable in principle to increase the specificity and the reliability of the action of active compounds. In particular, it is desirable for the crop protection product to control the harmful plants effectively and, at the same time, to be tolerated by the useful plants in question.

Various publications have described both 3-phenyluracils I and 3-sulfonylisoxazolines II as being highly effective herbicides. However, their compatibility with dicotyledonous crop plants such as cotton, oilseed rape and some graminaceous plants such as barley, millet, corn, rice, wheat and sugar cane is not always satisfactory, i.e. in addition to the harmful plants, the crop plants are also damaged to an extent which is not acceptable. It is possible to spare the useful plants by lowering the application rates; however the extent of the control of harmful plants is naturally also reduced.

It is known that certain combinations of different herbicides with specific action result in an enhanced activity of a herbicide component by synergism. As a consequence, it is possible to reduce the application rates of herbicidally active compounds required for controlling the harmful plants.

Furthermore, it is known that in some cases better crop plant compatibility can be achieved by joint application of specifically acting herbicides with organic active compounds, some of which are themselves herbicidally active. In these cases, the active compounds act as antidote or antagonist, and, owing to the fact that they can reduce or even prevent damage to the crop plants, they are also referred to as safeners.

3-Phenyluracils of Formula I

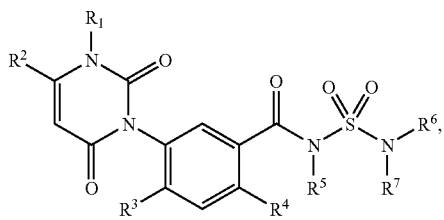

and their agriculturally acceptable salts are disclosed in the earlier patent application WO 01/83459. Certain herbicidal compositions of 3-phenyluracils of formula I are disclosed in the earlier patent applications WO 03/24221 and WO 04/80183.

3-Sulfonylisoxazolines of formula II

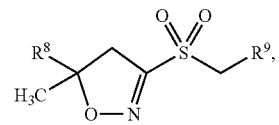

are disclosed in the earlier patent applications JP 09/328,483, WO 01/12613, WO 02/62770, WO 03/00686, WO 03/10165 and JP 2005/35924.

Certain herbicidal compositions of 3-sulfonylisoxazolines of formula II are disclosed in the earlier patent applications JP 2004/002324 and WO 04/14138.

It is an object of the present invention to increase the herbicidal activity of 3-phenyluracils of formula I and 3-sulfonylisoxazolines of formula II against undesirable harmful plants and to improve simultaneously their compatibility with useful plants.

We have found that this object is achieved, surprisingly, by compositions comprising
a) at least one 3-phenyluracil of formula I

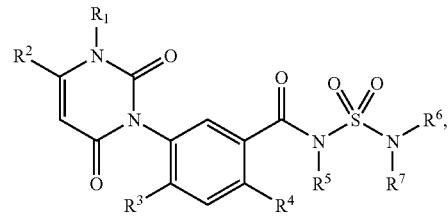

wherein the variables $R^1$ to $R^7$ are as defined below:
$R^1$ is methyl or $NH_2$;
$R^2$ is $C_1$-$C_2$-haloalkyl;
$R^3$ is hydrogen or halogen;
$R^4$ is halogen or cyano;
$R^5$ is hydrogen or $C_1$-$C_6$-alkyl;
$R^6$, $R^7$ independently of one another are hydrogen, $C_1$-$C_6$-alkyl, $C_1$-$C_6$-alkoxy, $C_3$-$C_6$-alkenyl, $C_3$-$C_6$-alkynyl, $C_3$-$C_7$-cycloalkyl, $C_3$-$C_7$-cycloalkenyl, phenyl or benzyl;
including their agriculturally acceptable salts;
b) at least one 3-sulfonylisoxazoline of formula II

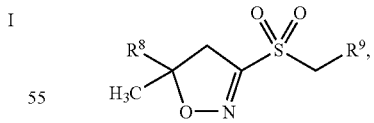

wherein the variables $R^8$ and $R^9$ are as defined below:
$R^8$ is $C_1$-$C_4$-alkyl or $C_1$-$C_4$-haloalkyl;
$R^9$ is phenyl, naphthyl, pyrazolyl, isoxazolyl or pyridyl, wherein each of the 5 aforementioned radicals may be unsubstituted or substituted by 1 to 6 halogen atoms and/or by 1, 2 or 3 substituents selected from the group consisting of cyano, $C_1$-$C_6$-alkyl, $C_1$-$C_4$-haloalkyl, $C_3$-$C_6$-alkenyl, $C_3$-$C_6$-alkynyl, $C_3$-$C_7$-cycloalkyl, $C_3$-$C_7$-cycloalkenyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl, $C_1$-$C_4$-alkylcarbonyl, $C_1$-$C_4$-alkoxycarbonyl, phenyl and benzyl; and c) optionally at least one safener III selected from the group consisting of benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1,3-oxazolidine, 4-(dichloroacetyl)-1-oxa-4-azaspiro[4.5]decane and oxabetrinil, including their agriculturally acceptable salts and, provided they have a carboxyl group, their agriculturally acceptable derivatives.

The invention relates in particular to compositions in the form of herbicidally active crop protection compositions comprising a herbicidally effective amount of at least one composition of I with II and optionally III, as defined above, and at least one liquid and/or solid carrier and, if desired, one or more surfactants and, if desired, one or more further auxiliaries customary for crop protection compositions.

The invention also relates to compositions in the form of a crop protection composition formulated as a 2-component composition comprising a first component which comprises the active compound I and optionally a safener II, a solid or liquid carrier and, if appropriate, one or more surfactants, and a second component which comprises at least one further herbicide II and optionally a safener II, a solid or liquid carrier and, if appropriate, one or more surfactants, where both components may additionally comprise further auxiliaries customary for crop protection compositions.

The invention furthermore relates to a method for controlling undesirable vegetation, which comprises applying a herbicidal composition according to the present invention before, during and/or after, preferably during and/or after, the emergence of the undesirable plants; the components I, II and optionally III being applied simultaneously or in succession.

The invention furthermore relates to a method for controlling undesirable vegetation, which comprises allowing a herbicidally effective amount of a composition according to the present invention to act on plants, their habitat or on seed.

The invention furthermore relates to a method for controlling undesirable vegetation in crops, in particular in crops of cereals, corn, soybeans, rice, oilseed rape, cotton, potatoes, groundnuts, preferably cereals, corn, soybeans or rice, or in perennial crops.

The invention furthermore relates to a method for controlling undesirable vegetation in crops which, by genetic engineering or by breeding, are resistant to one or more herbicides and/or fungicides, and/or to attack by insects; preferably resistant to one or more herbicides.

The invention also relates to a method for the desiccation or defoliation of plants. In the latter methods it is immaterial whether the herbicidally active compounds of components I and II and optionally III are formulated and applied jointly or separately, and, in the case of separate application, in which order the application takes place.

The organic moieties mentioned in the definition of the substituents $R^2$, $R^5$, $R^6$, $R^7$ in formula I or as substituents on phenyl, naphthyl, pyrazolyl, isoxazolyl or pyridyl rings in formula II are—like the term halogen—collective terms for individual enumerations of the individual group members. All hydrocarbon chains, i.e. all alkyl, haloalkyl, cycloalkyl, alkoxy, haloalkoxy, alkylamino, alkylthio, haloalkylthio, alkylsulfinyl, haloalkylsulfinyl, alkylsulfonyl, haloalkylsulfonyl, alkenyl and alkynyl groups and corresponding moieties in larger groups such as alkylcarbonyl, alkylaminocarbonyl, dialkylaminocarbonyl, alkoxycarbonyl, etc., can be straight-chain or branched, the prefix $C_n$-$C_m$ denoting in each case the possible number of carbon atoms in the group. Halogenated substituents preferably carry one, two, three, four or five identical or different halogen atoms. The term halogen denotes in each case fluorine, chlorine, bromine or iodine.

Examples of other meanings are:

$C_1$-$C_4$-alkyl: $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_2$-haloalkyl: a methyl or ethyl radical, which is partially or fully substituted by fluorine, chlorine, bromine and/or iodine, for example $CH_2F$, $CHF_2$, $CF_3$, $CH_2Cl$, dichloromethyl, trichloromethyl, chlorofluormethyl, dichlorofluoromethyl, chlorodifluoromethyl, 2-fluoroethyl, 2-chloroethyl, 2-brom-oethyl, 2-iodoethyl, 2,2-difluoroethyl, 2,2,2-trifluoroethyl, 2-chloro-2-fluor-oethyl, 2-chloro-2,2-difluoroethyl, 2,2-dichloro-2-fluoroethyl, 2,2,2-tri-chloroethyl, $C_2F_5$;

$C_1$-$C_4$-haloalkyl: a $C_1$-$C_4$-alkyl radical as mentioned above which is partially or fully substituted by fluorine, chlorine, bromine and/or iodine, i.e., for example, $CH_2F$, $CHF_2$, $CF_3$, $CH_2Cl$, dichloromethyl, trichloromethyl, chlorofluormethyl, dichlorofluoromethyl, chlorodifluoromethyl, 2-fluoroethyl, 2-chloroethyl, 2-brom-oethyl, 2-iodoethyl, 2,2-difluoroethyl, 2,2,2-trifluoroethyl, 2-chloro-2-fluor-oethyl, 2-chloro-2,2-difluoroethyl, 2,2-dichloro-2-fluoroethyl, 2,2,2-tri-chloroethyl, $C_2F_5$, 2-fluoropropyl, 3-fluoropropyl, 2,2-difluoropropyl, 2,3-difluoro-propyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$-$C_4$-alkoxy: $OCH_3$, $OC_2H_5$, n-propoxy, $OCH(CH_3)_2$, n-butoxy, $OCH(CH_3)$—$C_2H_5$, $OCH_2$—$CH(CH_3)_2$ or $OC(CH_3)_3$, preferably $OCH_3$, $OC_2H_5$ or $OCH(CH_3)_2$;

$C_1$-$C_6$-alkoxy: a $C_1$-$C_4$-alkoxy radical as mentioned above, and also, for example pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above, which is partially or fully substituted by fluorine, chlorine, bromine and/or iodine, i.e., for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$-$C_4$-alkylthio: $SCH_3$, $SC_2H_5$, n-propylthio, $SCH(CH_3)_2$, n-butylthio, $SCH(CH_3)$—$C_2H_5$, $SCH_2$—$CH(CH_3)_2$ or $SC(CH_3)_3$, preferably $SCH_3$ or $SC_2H_5$;

$C_1$-$C_4$-haloalkylthio: a $C_1$-$C_4$-alkylthio radical as mentioned above which is partially or fully substituted by fluorine, chlorine, bromine and/or iodine, i.e., for example, $SCH_2F$, $SCHF_2$, $SCH_2Cl$, $SCH(Cl)_2$, $SC(Cl)_3$, $SCF_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or $SCF_2$—$CF_2$—$C_2F_5$, preferably $SCHF_2$, $SCF_3$, dichlorofluoromethylthio, chlorodifluoromethylthio or 2,2,2-trifluoroethylthio;

($C_1$-$C_4$-alkyl)carbonyl: CO—$CH_3$, CO—$C_2H_5$, CO—$CH_2$—$C_2H_5$, CO—$CH(CH_3)_2$, n-butylcarbonyl, CO—$CH(CH_3)$—$C_2H_5$, CO—$CH_2$—$CH(CH_3)_2$ or CO—$C(CH_3)_3$, preferably CO—$CH_3$ or CO—$C_2H_5$;

($C_1$-$C_4$-alkoxy)carbonyl: CO—$OCH_3$, CO—$OC_2H_5$, n-propoxycarbonyl, CO—$OCH(CH_3)_2$, n-butoxycarbonyl, CO—$OCH(CH_3)$—$C_2H_5$, CO—$OCH_2$—$CH(CH_3)_2$ or CO—$OC(CH_3)_3$ preferably CO—$OCH_3$ or CO—$OC_2H_5$;

$C_1$-$C_4$ alkylsulfonyl: $SO_2$—$CH_3$, $SO_2$—$C_2H_5$, $SO_2$—$CH_2$—$C_2H_5$, $SO_2$—$CH(CH_3)_2$, n-butylsulfonyl, $SO_2$—$CH(CH_3)$—$C_2H_5$, $SO_2$—$CH_2$—$CH(CH_3)_2$ or $SO_2$—$C(CH_3)_3$, preferably $SO_2$—$CH_3$ or $SO_2$—$C_2H_5$;

$C_1$-$C_4$-haloalkylsulfonyl: a $C_1$-$C_4$-alkylsulfonyl radical—as mentioned above—which is partially or fully substituted by fluorine, chlorine, bromine and/or iodine, i.e., for example, $SO_2$—$CH_2F$, $SO_2$—$CHF_2$, $SO_2$—$CF_3$, $SO_2$—$CH_2Cl$, $SO_2$—$CH(Cl)_2$, $SO_2$—$C(Cl)_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, $SO_2$—$C_2F_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $SO_2$—$CH_2$—$C_2F_5$, $SO_2$—$CF_2$—$C_2F_5$, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl, preferably $SO_2$—$CF_3$, $SO_2$—$CH_2Cl$ or 2,2,2-trifluoroethylsulfonyl;

$C_3$-$C_6$-alkenyl: prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_3$-$C_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably prop-2-yn-1-yl;

$C_3$-$C_7$-cycloalkyl: a monocyclic saturated hydrocarbon ring having 3 to 7 ring members, such as cyclopropyl, cyclobutyl, cyclopentyl, cyclohexyl or cycloheptyl;

$C_3$-$C_7$-cycloalkenyl: monocyclic unsaturated hydrocarbon ring having 3 to 7 ring members, such as cycloprop-1-enyl, cycloprop-2-enyl, cyclobut-1-enyl, cyclobut-2-enyl, cyclobut-1,3-dienyl, cyclopent-1-enyl, cyclopent-2-enyl, cyclopent-3-enyl, cyclopent-2,4-dienyl, cyclohex-1-enyl, cyclohex-2-enyl, cyclohex-3-enyl; cyclohex-1,3-dienyl, cyclohex-1,5-dienyl, cyclohex-2,4-dienyl, or cyclohex-2,5-dienyl.

The active compounds III are known safeners, see, for example,

The Compendium of Pesticide Common Names (http://www.hclrss.demon.co.uk/index.html);

Farm Chemicals Handbook 2000 Vol. 86, Meister Publishing Company, 2000;

B. Hock, C. Fedtke, R. R. Schmidt, Herbizide, Georg Thieme Verlag, Stuttgart 1995;

W. H. Ahrens, Herbicide Handbook, 7th Edition, Weed Science Society of America, 1994; and K. K. Hatzios, Herbicide Handbook, Supplement to 7th Edition, Weed Science Society of America, 1998.

2,2,5-Trimethyl-3-(dichloroacetyl)-1,3-oxazolidine [CAS No. 52836-31-4] is also known under the name R-29148.

4-(Dichloroacetyl)-1-oxa-4-azaspiro[4.5]decane [CAS No. 71526-07-03] is also known under the names AD-67 and MON 4660.

If the 3-phenyluracils I, the 3-sulfonylisoxazolines II and/or the safeners III are capable of forming geometrical isomers, for example E/Z isomers, it is possible to use both the pure isomers and mixtures thereof in the compositions according to the invention. If the phenyluracils I, the 3-sulfonylisoxazolines II and/or the safeners III have one or more centers of chirality and, as a consequence, are present as enantiomers or diastereomers, it is possible to use both the pure enantiomers and diastereomers and their mixtures in the compositions according to the invention.

If the 3-phenyluracils I, the 3-sulfonylisoxazolines II and/or the safeners III have functional groups, which can be ionized, they can also be used in the form of their agriculturally acceptable salts. In general, the salts of those cations are suitable whose cations have no adverse effect on the action of the active compounds ("agricultural acceptable").

Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

It is possible to use, for example, the 3-phenyluracils of formula I and cloquintocet, fenchlorazole, isoxadifen and mefenpyr, if desired, as salts of the agriculturally useful cations mentioned above, in the compositions according to the invention.

In the compositions according to the invention, the safeners III which carry a carboxyl group can, instead of the active compounds mentioned above, also be employed in the form of an agriculturally acceptable derivative, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters. Examples of active compounds having a COOH group which can also be employed as derivatives are: cloquintocet, fenchlorazole, isoxadifen ad mefenpyr.

Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters.

Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester.

Preferred arylamides are, for example, the anilidines and the 2-chloroanilides.

Preferred alkyl esters are, for example, the methyl, ethyl, propyl, isopropyl, butyl, isobutyl, pentyl, mexyl (1-methylhexyl) or isooctyl (2-ethylhexyl) esters.

Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester.

Among the 3-phenyluracils of formula I, preference is given to those wherein the variables $R^1$ to $R^7$ independently of one another, but preferably combined, have the meanings given below:

$R^1$ is methyl or $NH_2$;

$R^2$ is trifluoromethyl;

$R^3$ is hydrogen, fluorine or chlorine, in particular fluorine;

$R^4$ is halogen or cyano,
  in particular chlorine or cyano;

$R^5$ is hydrogen;

$R^6$, $R^7$ independently of one another are hydrogen, $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkenyl, phenyl or benzyl;
  in particular hydrogen or $C_1$-$C_6$-alkyl.

$R^6$ and $R^7$ are in particular identical or different $C_1$-$C_6$-alkyl radicals, preferably identical or different $C_1$-$C_4$-alkyl radicals.

In a particularly preferred embodiment of the invention, the compositions comprise at least one 3-phenyluracil I in which the variables $R^1$ to $R^7$ in formula I have the following meanings (hereinbelow also referred to as 3-phenyluracils Ia):

$R^1$ is methyl;

$R^2$ is trifluoromethyl;

$R^3$ is fluorine;

$R^4$ is chlorine;

$R^5$ is hydrogen;

$R^6$, $R^7$ independently of one another are $C_1$-$C_6$-alkyl.

In another particularly preferred embodiment of the invention, the compositions comprise at least one 3-phenyluracil I in which the variables $R^1$ to $R^7$ in formula I have the meanings below (hereinbelow also referred to as 3-phenyluracils Ib):

$R^1$ is $NH_2$;

$R^2$ is trifluoromethyl;

$R^3$ is fluorine;

$R^4$ is chlorine;

$R^5$ is hydrogen;

$R^6$, $R^7$ independently of one another are $C_1$-$C_6$-alkyl.

Examples of particularly preferred 3-phenyluracils I, especially 3-phenyluracils Ia or Ib are the 3-phenyluracils I' listed below in wherein $R^1$, $R^6$ and $R^7$ together have the meanings given in one row of table 1 (compounds 1.1 to 1.74).

TABLE 1

3-phenyluracil I'

| 3-phenyluracil I' | R¹ | R⁶ | R⁷ |
|---|---|---|---|
| I.1 | methyl | methyl | methyl |
| I.2 | amino | methyl | methyl |
| I.3 | methyl | methyl | ethyl |
| I.4 | amino | methyl | ethyl |
| I.5 | methyl | methyl | propyl |
| I.6 | amino | methyl | propyl |
| I.7 | methyl | methyl | isopropyl |
| I.8 | amino | methyl | isopropyl |
| I.9 | methyl | methyl | butyl |
| I.10 | amino | methyl | butyl |
| I.11 | methyl | methyl | s-butyl |
| I.12 | amino | methyl | s-butyl |
| I.13 | methyl | methyl | isobutyl |
| I.14 | amino | methyl | isobutyl |
| I.15 | methyl | methyl | t-butyl |
| I.16 | amino | methyl | t-butyl |
| I.17 | methyl | methyl | n-pentyl |
| I.18 | amino | methyl | n-pentyl |
| I.19 | methyl | methyl | n-hexyl |
| I.20 | amino | methyl | n-hexyl |
| I.21 | methyl | methyl | allyl |
| I.22 | amino | methyl | allyl |
| I.23 | methyl | methyl | propargyl |
| I.24 | amino | methyl | propargyl |
| I.25 | methyl | methyl | phenyl |
| I.26 | amino | methyl | phenyl |
| I.27 | methyl | methyl | benzyl |
| I.28 | amino | methyl | benzyl |
| I.29 | methyl | ethyl | ethyl |
| I.30 | amino | ethyl | ethyl |
| I.31 | methyl | ethyl | propyl |
| I.32 | amino | ethyl | propyl |
| I.33 | methyl | ethyl | isopropyl |
| I.34 | amino | ethyl | isopropyl |
| I.35 | methyl | ethyl | butyl |
| I.36 | amino | ethyl | butyl |
| I.37 | methyl | ethyl | n-pentyl |
| I.38 | amino | ethyl | n-pentyl |
| I.39 | methyl | ethyl | n-hexyl |
| I.40 | amino | ethyl | n-hexyl |
| I.41 | methyl | propyl | propyl |
| I.42 | amino | propyl | propyl |
| I.43 | methyl | propyl | isopropyl |
| I.44 | amino | propyl | isopropyl |
| I.45 | methyl | propyl | butyl |
| I.46 | amino | propyl | butyl |
| I.47 | methyl | propyl | n-pentyl |
| I.48 | amino | propyl | n-pentyl |
| I.49 | methyl | propyl | n-hexyl |
| I.50 | amino | propyl | n-hexyl |
| I.51 | methyl | isopropyl | isopropyl |
| I.52 | amino | isopropyl | isopropyl |
| I.53 | methyl | isopropyl | butyl |
| I.54 | amino | isopropyl | butyl |
| I.55 | methyl | isopropyl | n-pentyl |
| I.56 | amino | isopropyl | n-pentyl |
| I.57 | methyl | isopropyl | n-hexyl |
| I.58 | amino | isopropyl | n-hexyl |
| I.59 | methyl | butyl | butyl |
| I.60 | amino | butyl | butyl |
| I.61 | methyl | butyl | n-pentyl |
| I.62 | amino | butyl | n-pentyl |
| I.63 | methyl | butyl | n-hexyl |
| I.64 | amino | butyl | n-hexyl |
| I.65 | methyl | n-pentyl | n-pentyl |
| I.66 | amino | n-pentyl | n-pentyl |
| I.67 | methyl | n-pentyl | n-hexyl |
| I.68 | amino | n-pentyl | n-hexyl |
| I.69 | methyl | n-hexyl | n-hexyl |
| I.70 | amino | n-hexyl | n-hexyl |
| I.71 | methyl | —(CH₂)₄— | |
| I.72 | amino | —(CH₂)₄— | |
| I.73 | methyl | —(CH₂)₂—O—(CH₂)₂— | |
| I.74 | amino | —(CH₂)₂—O—(CH₂)₂— | |

Among the 3-sulfonylisoxazolines of formula II, preference is given to those wherein the variable $R^8$ is methyl or chloromethyl.

Preference is also given to the 3-sulfonylisoxazolines of formula II wherein $R^8$ is $C_1$-$C_4$-alkyl, preferably methyl.

Preference is also given to those 3-sulfonylisoxazolines of formula II wherein $R^9$ is phenyl, naphthyl, isoxazolyl or pyridyl;
  particularly preferred phenyl, 1-naphthyl, 2-naphthyl, 3-isoxazolyl, 4-isoxazolyl, 2-pyridyl, 3-pyridyl or 4-pyridyl;
  especially preferred phenyl, 1-naphthyl or 2-naphthyl;
  very particular preferably phenyl;
  wherein each of the aforementioned radicals may be unsubstituted or substituted by 1 to 6 halogen atoms and/or by 1, 2 or 3 substituents selected from the group consisting of cyano, $C_1$-$C_6$-alkyl, $C_1$-$C_4$-haloalkyl, $C_3$-$C_6$-alkenyl, $C_3$-$C_6$-alkynyl, $C_3$-$C_7$-cycloalkyl, $C_3$-$C_7$-cycloalkenyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl, $C_1$-$C_4$-alkylcarbonyl, $C_1$-$C_4$-alkoxycarbonyl, phenyl and benzyl;
  particularly preferred unsubstituted or substituted by 1 to 3 halogen atoms or 1, 2 or 3 substituents selected from the group consisting of $C_1$-$C_6$-alkyl, $C_1$-$C_4$-haloalkyl, $C_1$-$C_4$-alkoxy, $C_1$-$C_4$-haloalkoxy, phenyl and benzyl;
  especially preferred unsubstituted or substituted by 1 to 3 halogen atoms or 1, 2 or 3 substituents selected from the group consisting of $C_1$-$C_6$-alkyl, $C_1$-$C_4$-haloalkyl and $C_1$-$C_4$-haloalkoxy;
  very particular preferred unsubstituted or substituted by 1 to 3 halogen atoms.

Preference is also given to those 3-sulfonylisoxazolines of formula II wherein $R^9$ is phenyl, naphthyl, isoxazolyl or pyridyl;
  particularly preferred phenyl, 1-naphthyl, 2-naphthyl, 3-isoxazolyl, 4-isoxazolyl, 2-pyridyl, 3-pyridyl or 4-pyridyl;
  especially preferred phenyl, 1-naphthyl or 2-naphthyl;
  very particular preferably phenyl;
  wherein each of the aforementioned radicals may be unsubstituted or substituted by 1 to 6 halogen atoms and/or by 1, 2 or 3 substituents selected from the group consisting of cyano, $C_1$-$C_6$-alkyl, $C_1$-$C_4$-haloalkyl, $C_3$-$C_6$-alkenyl, $C_3$-$C_6$-alkynyl, $C_3$-$C_7$-cycloalkyl, $C_3$-$C_7$-cycloalkenyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl, $C_1$-$C_4$-alkylcarbonyl, $C_1$-$C_4$-alkoxycarbonyl, phenyl and benzyl;

particularly preferred substituted by 1 to 3 halogen atoms or 1, 2 or 3 substituents selected from the group consisting of $C_1$-$C_6$-alkyl, $C_1$-$C_4$-haloalkyl, $C_1$-$C_4$-alkoxy, $C_1$-$C_4$-haloalkoxy, phenyl and benzyl;

especially preferred substituted by 1 to 3 halogen atoms or 1, 2 or 3 substituents selected from the group consisting of $C_1$-$C_6$-alkyl, $C_1$-$C_4$-haloalkyl and $C_1$-$C_4$-haloalkoxy;

very particular preferred substituted by 1 to 3 halogen atoms.

Preference is also given to those 3-sulfonylisoxazolines of formula II wherein $R^9$ is phenyl, 1-naphthyl, 2-naphthyl, 3-pyrazolyl, 4-pyrazolyl, 5-pyrazolyl, 3-isoxazolyl, 4-isoxazolyl, 2-pyridyl, 3-pyridyl or 4-pyridyl;

particularly preferred phenyl or 4-pyrazolyl;

wherein each of the aforementioned radicals may be unsubstituted or substituted by 1 to 6 halogen atoms and/or by 1, 2 or 3 substituents selected from the group consisting of cyano, $C_1$-$C_6$-alkyl, $C_1$-$C_4$-haloalkyl, $C_3$-$C_6$-alkenyl, $C_3$-$C_6$-alkynyl, $C_3$-$C_7$-cycloalkyl, $C_3$-$C_7$-cycloalkenyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkysulfonyl, $C_1$-$C_4$-haloalkylsulfonyl, $C_1$-$C_4$-alkylcarbonyl, $C_1$-$C_4$-alkoxycarbonyl, phenyl and benzyl;

particularly preferred unsubstituted or substituted by 1 to 3 halogen atoms and/or 1, 2 or 3 substituents selected from the group consisting of $C_1$-$C_6$-alkyl, $C_1$-$C_4$-haloalkyl, $C_1$-$C_4$-alkoxy, $C_1$-$C_4$-haloalkoxy, phenyl and benzyl;

especially preferred unsubstituted or substituted by 1 to 3 halogen atoms and/or 1, 2 or 3 substituents selected from the group consisting of $C_1$-$C_6$-alkyl, $C_1$-$C_4$-haloalkyl and $C_1$-$C_4$-haloalkoxy.

Preference is also given to those 3-sulfonylisoxazolines of formula II wherein $R^9$ is phenyl, 1-naphthyl, 2-naphthyl, 3-pyrazolyl, 4-pyrazolyl, 5-pyrazolyl, 3-isoxazolyl, 4-isoxazolyl, 2-pyridyl, 3-pyridyl or 4-pyridyl;

particularly preferred phenyl or 4-pyrazolyl;

wherein each of the aforementioned radicals may be unsubstituted or substituted by 1 to 6 halogen atoms and/or by 1, 2 or 3 substituents selected from the group consisting of cyano, $C_1$-$C_6$-alkyl, $C_1$-$C_4$-haloalkyl, $C_3$-$C_6$-alkenyl, $C_3$-$C_6$-alkynyl, $C_3$-$C_7$-cycloalkyl, $C_3$-$C_7$-cycloalkenyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkysulfonyl, $C_1$-$C_4$-haloalkylsulfonyl, $C_1$-$C_4$-alkylcarbonyl, $C_1$-$C_4$-alkoxycarbonyl, phenyl and benzyl;

particularly preferred substituted by 1 to 3 halogen atoms and/or 1, 2 or 3 substituents selected from the group consisting of $C_1$-$C_6$-alkyl, $C_1$-$C_4$-haloalkyl, $C_1$-$C_4$-alkoxy, $C_1$-$C_4$-haloalkoxy, phenyl and benzyl;

especially preferred substituted by 1 to 3 halogen atoms and/or 1, 2 or 3 substituents selected from the group consisting of $C_1$-$C_6$-alkyl, $C_1$-$C_4$-haloalkyl and $C_1$-$C_4$-haloalkoxy.

Preference is also given to those 3-sulfonylisoxazolines of formula II wherein the variables $R^8$ and $R^9$ have the meanings given below:

$R^8$ is $C_1$-$C_4$-alkyl;

$R^9$ is phenyl or 4-pyrazolyl, wherein each of the aforementioned two radicals may be unsubstituted or substituted by 1 to 3 halogen atoms and/or by 1 or 2 substituents selected from the group consisting of $C_1$-$C_4$-alkyl, $C_1$-$C_4$-haloalkyl, $C_1$-$C_4$-alkoxy, $C_1$-$C_4$-haloalkoxy, phenyl and benzyl.

Preference is also given to those 3-sulfonylisoxazolines of formula II wherein $R^8$ is $C_1$-$C_4$-alkyl or $C_1$-$C_4$-haloalkyl, preferably methyl or chloromethyl, especially preferred methyl; and $R^9$ is phenyl or 4-pyrazolyl, wherein each of the aforementioned two radicals may be unsubstituted or substituted by 1 to 3 halogen atoms and/or by 1 to 3 substituents selected from the group consisting of $C_1$-$C_4$-alkyl, $C_1$-$C_4$-haloalkyl, $C_1$-$C_4$-alkoxy, $C_1$-$C_4$-haloalkoxy, phenyl and benzyl;

preferably substituted by 1 to 3 halogen atoms and/or by 1 to 3 substituents selected from the group consisting of $C_1$-$C_4$-alkyl, $C_1$-$C_4$-haloalkyl and $C_1$-$C_4$-haloalkoxy.

In a particular preferred embodiment of the invention, the compositions comprise at least one 3-sulfonylisoxazoline II wherein the variables $R^8$ and $R^9$ have the following meanings (hereinbelow also referred to as 3-sulfonylisoxazolines IIa):

$R^8$ is $C_1$-$C_4$-alkyl or $C_1$-$C_4$-haloalkyl, preferably $C_1$-$C_4$-alkyl, especially preferred methyl;

$R^9$ is phenyl, which is substituted by 1 to 3 halogen atoms.

In another particularly preferred embodiment of the invention, the compositions comprise at least one 3-sulfonylisoxazoline II wherein the variables $R^8$ and $R^9$ have the following meanings (hereinbelow also referred to as 3-sulfonylisoxazolines IIb):

$R^8$ is $C_1$-$C_4$-alkyl or $C_1$-$C_4$-haloalkyl, preferably $C_1$-$C_4$-alkyl, especially preferred methyl;

$R^9$ is 4-pyrazolyl, which is substituted by 1 or 2 halogen atoms and/or 1 or 2 substituents selected from the group consisting of methyl, trifluoromethyl, difluoromethoxy or phenyl.

In another particularly preferred embodiment of the invention, the compositions comprise at least one 3-sulfonylisoxazoline II wherein the variables $R^8$ and $R^9$ have the following meanings (hereinbelow also referred to as 3-sulfonylisoxazolines IIc):

$R^8$ is $C_1$-$C_4$-alkyl or $C_1$-$C_4$-haloalkyl, preferably $C_1$-$C_4$-alkyl, especially preferred methyl;

$R^9$ is 4-pyrazolyl, which is substituted by 1 or 2 halogen atoms and/or 1 to 3 substituents selected from the groups consisting of methyl, trifluoromethyl, difluoromethoxy or phenyl.

Examples of particularly preferred 3-sulfonylisoxazolines II, especially 3-sulfonylisoxazolines IIa, IIb or IIc are the 3-sulfonylisoxazolines of the formula II' listed below wherein $R^8$ is methyl and $R^9$ has the meanings given in one row of table 2 (compounds II.1 to II.7).

TABLE 2

3-sulfonylisoxazoline II'

[Structure: isoxazoline ring with two methyl groups on C5, sulfonyl group (SO2) at C3 connected to CH2-R9]

| 3-sulfonylisoxazoline II' | $R^9$ |
|---|---|
| II.1 | 2,6-difluorophenyl |
| II.2 | 2-fluorophenyl |
| II.3 | 5-chloro-2-nitrophenyl |
| II.4 | 1-methyl-3-trifluoromethyl-1H-pyrazol-4-yl |
| II.5 | 5-difluoromethoxy-1-methyl-3-trifluoromethyl-1H-pyrazol-4-yl |
| II.6 | 5-chloro-1-methyl-3-trifluoromethyl-1H-pyrazol-4-yl |
| II.7 | 5-chloro-1-phenyl-3-trifluoromethyl-1H-pyrazol-4-yl |

As safener III, the compositions according to the invention particularly preferably comprise at least one of the compounds listed below: benoxacor, cloquintocet, dichlormid, fenchlorazole, fenclorim, fluxofenim, furilazole, isoxadifen, mefenpyr, naphthalic anhydride, 2,2,5-trimethyl-3-(dichloroacetyl)-1,3-oxazolidine, 4-(dichloroacetyl)-1-oxa-4-azaspiro[4.5]decane and oxabetrinil; and/or an agriculturally acceptable salt thereof and/or, in the case of compounds having a COOH group, an agriculturally acceptable derivative.

Particular preference is given to those binary and ternary compositions which comprise at least one 3-phenyluracil of formula I and at least one 3-sulfonylisoxazoline of formula II and, if appropriate, one or more safeners III.

Here and below, the term "binary compositions" includes compositions which comprise one or more (for example 2 or 3) 3-phenyluracils I and one or more (for example 2 or 3) 3-sulfonylisoxazolines II.

Correspondingly, the term "ternary compositions" includes compositions which comprise one or more (for example 2 or 3) 3-phenyluracils I, one or more (for example 2 or 3) 3-sulfonylisoxazolines II and one or more (for example 2 or 3) safeners III.

In binary compositions the weight ratio of the active compounds I:II is usually in the range from 1:10 to 10:1, preferably in the range from 1:5 to 5:1, in particular in the range from 1:3 to 3:1.

In ternary compositions which comprise both a 3-phenyluracil I, at least one 3-sulfonylisoxazoline II and at least one safener II, the relative weight ratios of the components I:II:III are usually in the range from 10:1:1 to 1:10:10, preferably from 5:1:1 to 1:5:5, in particular from 3:1:1 to 1:3:3.

In these ternary compositions, the weight ratio of 3-sulfonylisoxazoline II to safener III is preferably in the range from 10:1 to 1:10.

In a particular preferred embodiment of the invention, preference is given to those compositions of the invention which comprise
a) a 3-phenyluracil of the formula I, especially of formula Ia or Ib; in combination with
b) at least one, especially exactly one 3-sulfonylisoxazoline of formula II, especially of formula IIa, IIb or IIc; and
c) optionally a safener II, in particular selected from the group consisting of benoxacor, dichlormid, fenclorim, fluxofenim, furilazole, naphthalic anhydride, 2,2,5-trimethyl-3-(dichloroacetyl)-1,3-oxazolidine, 4-(dichloroacetyl)-1-oxa-4-azaspiro[4.5]decane and oxabetrinil.

In another particular preferred embodiment of the invention, preference is given to those compositions of the invention which comprise
a) a 3-phenyluracil of formula Ia; in combination with
b) a 3-sulfonylisoxazoline of formula IIa; and
c) optionally a safener II, in particular selected from the group consisting of benoxacor, dichlormid, fenclorim, fluxofenim, furilazole, naphthalic anhydride, 2,2,5-trimethyl-3-(dichloroacetyl)-1,3-oxazolidine, 4-(dichloroacetyl)-1-oxa-4-azaspiro[4.5]decane and oxabetrinil.

In another particular preferred embodiment of the invention, preference is given to those compositions of the invention which comprise
a) a 3-phenyluracil of formula Ia; in combination with
b) a 3-sulfonylisoxazoline of formula IIb; and
c) optionally a safener III, in particular selected from the group consisting of benoxacor, dichlormid, fenclorim, fluxofenim, furilazole, naphthalic anhydride, 2,2,5-trimethyl-3-(dichloroacetyl)-1,3-oxazolidine, 4-(dichloroacetyl)-1-oxa-4-azaspiro[4.5]decane and oxabetrinil.

In another particular preferred embodiment of the invention, preference is given to those compositions of the invention which comprise
a) a 3-phenyluracil of formula Ia; in combination with
b) a 3-sulfonylisoxazoline of formula IIc; and
c) optionally a safener II, in particular selected from the group consisting of benoxacor, dichlormid, fenclorim, fluxofenim, furilazole, naphthalic anhydride, 2,2,5-trimethyl-3-(dichloroacetyl)-1,3-oxazolidine, 4-(dichloroacetyl)-1-oxa-4-azaspiro[4.5]decane and oxabetrinil.

In the preferred or especially preferred compositions described above the 3-phenyluracils I and the safeners III can be used in the form of their agriculturally acceptable salts or in the form of an agriculturally acceptable derivative thereof as described above.

The weight ratios of the individual components in the compositions are within the limits stated above.

Among the especially preferred compositions, particular preference is given to those compositions of the invention wherein the variables $R^1$ to $R^7$ have the preferred meanings, especially the particularly preferred meanings. Particular preference is given to 3-phenyluracils of formula Ia and Ib, and to 3-sulfonylisoxazolines of formula IIa, IIb and IIc as defined above.

Preference is given, for example, to those compositions which, as active compound I, comprise the phenyluracil I.1 and, as further active compound, the substances listed in one row of table 3 (compositions 1.1 to 1.70). The weight ratios of the individual components in the compositions 1.1 to 1.70 are within the stated limits, in the case of binary compositions of phenyluracil I.1 and 3-sulfonylisoxazoline II for example 1:1, and in the case of ternary compositions of phenyluracil I.1, 3-sulfonylisoxazoline II and safener III for example 1:1:1, 2:1:1, 1:2:1, 1:5:1 or 1:5:2.

TABLE 3

| composition no. | 3-sulfonyl-isoxazoline II | safener III |
|---|---|---|
| 1.1 | II.1 | — |
| 1.2 | II.1 | benoxacor |
| 1.3 | II.1 | dichlormid |
| 1.4 | II.1 | fenclorim |
| 1.5 | II.1 | fluxofenim |
| 1.6 | II.1 | furilazole |
| 1.7 | II.1 | naphthalic anhydride |
| 1.8 | II.1 | 2,2,5-trimethyl-3-(dichloroacetyl)-1,3-oxazolidine |
| 1.9 | II.1 | 4-(dichloroacetyl)-1-oxa-4-azaspiro[4.5]decane |
| 1.10 | II.1 | oxabetrinil |
| 1.11 | II.2 | — |
| 1.12 | II.2 | benoxacor |
| 1.13 | II.2 | dichlormid |
| 1.14 | II.2 | fenclorim |
| 1.15 | II.2 | fluxofenim |
| 1.16 | II.2 | furilazole |
| 1.17 | II.2 | naphthalic anhydride |
| 1.18 | II.2 | 2,2,5-trimethyl-3-(dichloroacetyl)-1,3-oxazolidine |
| 1.19 | II.2 | 4-(dichloroacetyl)-1-oxa-4-azaspiro[4.5]decane |
| 1.20 | II.2 | oxabetrinil |
| 1.21 | II.3 | — |
| 1.22 | II.3 | benoxacor |
| 1.23 | II.3 | dichlormid |
| 1.24 | II.3 | fenclorim |
| 1.25 | II.3 | fluxofenim |
| 1.26 | II.3 | furilazole |
| 1.27 | II.3 | naphthalic anhydride |
| 1.28 | II.3 | 2,2,5-trimethyl-3-(dichloroacetyl)-1,3-oxazolidine |
| 1.29 | II.3 | 4-(dichloroacetyl)-1-oxa-4-azaspiro[4.5]decane |
| 1.30 | II.3 | oxabetrinil |
| 1.31 | II.4 | — |
| 1.32 | II.4 | benoxacor |
| 1.33 | II.4 | dichlormid |
| 1.34 | II.4 | fenclorim |
| 1.35 | II.4 | fluxofenim |
| 1.36 | II.4 | furilazole |
| 1.37 | II.4 | naphthalic anhydride |
| 1.38 | II.4 | 2,2,5-trimethyl-3-(dichloroacetyl)-1,3-oxazolidine |
| 1.39 | II.4 | 4-(dichloroacetyl)-1-oxa-4-azaspiro[4.5]decane |
| 1.40 | II.4 | oxabetrinil |
| 1.41 | II.5 | — |
| 1.42 | II.5 | benoxacor |
| 1.43 | II.5 | dichlormid |
| 1.44 | II.5 | fenclorim |
| 1.45 | II.5 | fluxofenim |
| 1.46 | II.5 | furilazole |
| 1.47 | II.5 | naphthalic anhydride |
| 1.48 | II.5 | 2,2,5-trimethyl-3-(dichloroacetyl)-1,3-oxazolidine |
| 1.49 | II.5 | 4-(dichloroacetyl)-1-oxa-4-azaspiro[4.5]decane |
| 1.50 | II.5 | oxabetrinil |
| 1.51 | II.6 | — |
| 1.52 | II.6 | benoxacor |
| 1.53 | II.6 | dichlormid |
| 1.54 | II.6 | fenclorim |
| 1.55 | II.6 | fluxofenim |
| 1.56 | II.6 | furilazole |
| 1.57 | II.6 | naphthalic anhydride |
| 1.58 | II.6 | 2,2,5-trimethyl-3-(dichloroacetyl)-1,3-oxazolidine |
| 1.59 | II.6 | 4-(dichloroacetyl)-1-oxa-4-azaspiro[4.5]decane |
| 1.60 | II.6 | oxabetrinil |
| 1.61 | II.7 | — |
| 1.62 | II.7 | benoxacor |
| 1.63 | II.7 | dichlormid |
| 1.64 | II.7 | fenclorim |
| 1.65 | II.7 | fluxofenim |
| 1.66 | II.7 | furilazole |
| 1.67 | II.7 | naphthalic anhydride |
| 1.68 | II.7 | 2,2,5-trimethyl-3-(dichloroacetyl)-1,3-oxazolidine |
| 1.69 | II.7 | 4-(dichloroacetyl)-1-oxa-4-azaspiro[4.5]decane |
| 1.70 | II.7 | oxabetrinil |

Preference is also given to the compositions 2.1-2.70 which differ from the corresponding compositions 1.1-1.70 only in that the phenyluracil I.1 is replaced by the phenyluracil I.2.

Preference is also given to the compositions 3.1-3.70 which differ from the corresponding compositions 1.1-1.70 only in that the phenyluracil I.1 is replaced by the phenyluracil I.3.

Preference is also given to the compositions 4.1-4.70 which differ from the corresponding compositions 1.1-1.70 only in that the phenyluracil I.1 is replaced by the phenyluracil I.4.

Preference is also given to the compositions 5.1-5.70 which differ from the corresponding compositions 1.1-1.70 only in that the phenyluracil I.1 is replaced by the phenyluracil I.5.

Preference is also given to the compositions 6.1-6.70 which differ from the corresponding compositions 1.1-1.70 only in that the phenyluracil I.1 is replaced by the phenyluracil I.6.

Preference is also given to the compositions 7.1-7.70 which differ from the corresponding compositions 1.1-1.70 only in that the phenyluracil I.1 is replaced by the phenyluracil I.7.

Preference is also given to the compositions 8.1-8.70 which differ from the corresponding compositions 1.1-1.70 only in that the phenyluracil I.1 is replaced by the phenyluracil I.8.

Preference is also given to the compositions 9.1-9.70 which differ from the corresponding compositions 1.1-1.70 only in that the phenyluracil I.1 is replaced by the phenyluracil I.9.

Preference is also given to the compositions 10.1-10.70 which differ from the corresponding compositions 1.1-1.70 only in that the phenyluracil I.1 is replaced by the phenyluracil I.10.

Preference is also given to the compositions 11.1-11.70 which differ from the corresponding compositions 1.1-1.70 only in that the phenyluracil I.1 is replaced by the phenyluracil I.11.

Preference is also given to the compositions 12.1-12.70 which differ from the corresponding compositions 1.1-1.70 only in that the phenyluracil I.1 is replaced by the phenyluracil I.12.

Preference is also given to the compositions 13.1-13.70 which differ from the corresponding compositions 1.1-1.70 only in that the phenyluracil I.1 is replaced by the phenyluracil I.13.

Preference is also given to the compositions 14.1-14.70 which differ from the corresponding compositions 1.1-1.70 only in that the phenyluracil I.1 is replaced by the phenyluracil I.14.

Preference is also given to the compositions 15.1-15.70 which differ from the corresponding compositions 1.1-1.70 only in that the phenyluracil I.1 is replaced by the phenyluracil I.15.

Preference is also given to the compositions 16.1-16.70 which differ from the corresponding compositions 1.1-1.70 only in that the phenyluracil I.1 is replaced by the phenyluracil I.16.

Preference is also given to the compositions 17.1-17.70 which differ from the corresponding compositions 1.1-1.70 only in that the phenyluracil I.1 is replaced by the phenyluracil I.17.

Preference is also given to the compositions 18.1-18.70 which differ from the corresponding compositions 1.1-1.70 only in that the phenyluracil I.1 is replaced by the phenyluracil I.18.

Preference is also given to the compositions 19.1-19.70 which differ from the corresponding compositions 1.1-1.70 only in that the phenyluracil I.1 is replaced by the phenyluracil I.19.

Preference is also given to the compositions 20.1-20.70 which differ from the corresponding compositions 1.1-1.70 only in that the phenyluracil I.1 is replaced by the phenyluracil I.20.

Preference is also given to the compositions 21.1-21.70 which differ from the corresponding compositions 1.1-1.70 only in that the phenyluracil I.1 is replaced by the phenyluracil I.21.

Preference is also given to the compositions 22.1-22.70 which differ from the corresponding compositions 1.1-1.70 only in that the phenyluracil I.1 is replaced by the phenyluracil I.22.

Preference is also given to the compositions 23.1-23.70 which differ from the corresponding compositions 1.1-1.70 only in that the phenyluracil I.1 is replaced by the phenyluracil I.23.

Preference is also given to the compositions 24.1-24.70 which differ from the corresponding compositions 1.1-1.70 only in that the phenyluracil I.1 is replaced by the phenyluracil I.24.

Preference is also given to the compositions 25.1-25.70 which differ from the corresponding compositions 1.1-1.70 only in that the phenyluracil I.1 is replaced by the phenyluracil I.25.

Preference is also given to the compositions 26.1-26.70 which differ from the corresponding compositions 1.1-1.70 only in that the phenyluracil I.1 is replaced by the phenyluracil I.26.

Preference is also given to the compositions 27.1-27.70 which differ from the corresponding compositions 1.1-1.70 only in that the phenyluracil I.1 is replaced by the phenyluracil I.27.

Preference is also given to the compositions 28.1-28.70 which differ from the corresponding compositions 1.1-1.70 only in that the phenyluracil I.1 is replaced by the phenyluracil I.28.

Preference is also given to the compositions 29.1-29.70 which differ from the corresponding compositions 1.1-1.70 only in that the phenyluracil I.1 is replaced by the phenyluracil I.29.

Preference is also given to the compositions 30.1-30.70 which differ from the corresponding compositions 1.1-1.70 only in that the phenyluracil I.1 is replaced by the phenyluracil I.30.

Preference is also given to the compositions 31.1-31.70 which differ from the corresponding compositions 1.1-1.70 only in that the phenyluracil I.1 is replaced by the phenyluracil I.31.

Preference is also given to the compositions 32.1-32.70 which differ from the corresponding compositions 1.1-1.70 only in that the phenyluracil I.1 is replaced by the phenyluracil I.32.

Preference is also given to the compositions 33.1-33.70 which differ from the corresponding compositions 1.1-1.70 only in that the phenyluracil I.1 is replaced by the phenyluracil I.33.

Preference is also given to the compositions 34.1-34.70 which differ from the corresponding compositions 1.1-1.70 only in that the phenyluracil I.1 is replaced by the phenyluracil I.34.

Preference is also given to the compositions 35.1-35.70 which differ from the corresponding compositions 1.1-1.70 only in that the phenyluracil I.1 is replaced by the phenyluracil I.35.

Preference is also given to the compositions 36.1-36.70 which differ from the corresponding compositions 1.1-1.70 only in that the phenyluracil I.1 is replaced by the phenyluracil I.36.

Preference is also given to the compositions 37.1-37.70 which differ from the corresponding compositions 1.1-1.70 only in that the phenyluracil I.1 is replaced by the phenyluracil I.37.

Preference is also given to the compositions 38.1-38.70 which differ from the corresponding compositions 1.1-1.70 only in that the phenyluracil I.1 is replaced by the phenyluracil I.38.

Preference is also given to the compositions 39.1-39.70 which differ from the corresponding compositions 1.1-1.70 only in that the phenyluracil I.1 is replaced by the phenyluracil I.39.

Preference is also given to the compositions 40.1-40.70 which differ from the corresponding compositions 1.1-1.70 only in that the phenyluracil I.1 is replaced by the phenyluracil I.40.

Preference is also given to the compositions 41.1-41.70 which differ from the corresponding compositions 1.1-1.70 only in that the phenyluracil I.1 is replaced by the phenyluracil I.41.

Preference is also given to the compositions 42.1-42.70 which differ from the corresponding compositions 1.1-1.70 only in that the phenyluracil I.1 is replaced by the phenyluracil I.42.

Preference is also given to the compositions 43.1-43.70 which differ from the corresponding compositions 1.1-1.70 only in that the phenyluracil I.1 is replaced by the phenyluracil I.43.

Preference is also given to the compositions 44.1-44.70 which differ from the corresponding compositions 1.1-1.70 only in that the phenyluracil I.1 is replaced by the phenyluracil I.44.

Preference is also given to the compositions 45.1-45.70 which differ from the corresponding compositions 1.1-1.70 only in that the phenyluracil I.1 is replaced by the phenyluracil I.45.

Preference is also given to the compositions 46.1-46.70 which differ from the corresponding compositions 1.1-1.70 only in that the phenyluracil I.1 is replaced by the phenyluracil I.46.

Preference is also given to the compositions 47.1-47.70 which differ from the corresponding compositions 1.1-1.70 only in that the phenyluracil I.1 is replaced by the phenyluracil I.47.

Preference is also given to the compositions 48.1-48.70 which differ from the corresponding compositions 1.1-1.70 only in that the phenyluracil I.1 is replaced by the phenyluracil I.48.

Preference is also given to the compositions 49.1-49.70 which differ from the corresponding compositions 1.1-1.70 only in that the phenyluracil I.1 is replaced by the phenyluracil I.49.

Preference is also given to the compositions 50.1-50.70 which differ from the corresponding compositions 1.1-1.70 only in that the phenyluracil I.1 is replaced by the phenyluracil I.50.

Preference is also given to the compositions 51.1-51.70 which differ from the corresponding compositions 1.1-1.70 only in that the phenyluracil I.1 is replaced by the phenyluracil I.51.

Preference is also given to the compositions 52.1-52.70 which differ from the corresponding compositions 1.1-1.70 only in that the phenyluracil I.1 is replaced by the phenyluracil I.52.

Preference is also given to the compositions 53.1-53.70 which differ from the corresponding compositions 1.1-1.70 only in that the phenyluracil I.1 is replaced by the phenyluracil I.53.

Preference is also given to the compositions 54.1-54.70 which differ from the corresponding compositions 1.1-1.70 only in that the phenyluracil I.1 is replaced by the phenyluracil I.54.

Preference is also given to the compositions 55.1-55.70 which differ from the corresponding compositions 1.1-1.70 only in that the phenyluracil I.1 is replaced by the phenyluracil I.55.

Preference is also given to the compositions 56.1-56.70 which differ from the corresponding compositions 1.1-1.70 only in that the phenyluracil I.1 is replaced by the phenyluracil I.56.

Preference is also given to the compositions 57.1-57.70 which differ from the corresponding compositions 1.1-1.70 only in that the phenyluracil I.1 is replaced by the phenyluracil I.57.

Preference is also given to the compositions 58.1-58.70 which differ from the corresponding compositions 1.1-1.70 only in that the phenyluracil I.1 is replaced by the phenyluracil I.58.

Preference is also given to the compositions 59.1-59.70 which differ from the corresponding compositions 1.1-1.70 only in that the phenyluracil I.1 is replaced by the phenyluracil I.59.

Preference is also given to the compositions 60.1-60.70 which differ from the corresponding compositions 1.1-1.70 only in that the phenyluracil I.1 is replaced by the phenyluracil I.60.

Preference is also given to the compositions 61.1-61.70 which differ from the corresponding compositions 1.1-1.70 only in that the phenyluracil I.1 is replaced by the phenyluracil I.61.

Preference is also given to the compositions 62.1-62.70 which differ from the corresponding compositions 1.1-1.70 only in that the phenyluracil I.1 is replaced by the phenyluracil I.62.

Preference is also given to the compositions 63.1-63.70 which differ from the corresponding compositions 1.1-1.70 only in that the phenyluracil I.1 is replaced by the phenyluracil I.63.

Preference is also given to the compositions 64.1-64.70 which differ from the corresponding compositions 1.1-1.70 only in that the phenyluracil I.1 is replaced by the phenyluracil I.64.

Preference is also given to the compositions 65.1-65.70 which differ from the corresponding compositions 1.1-1.70 only in that the phenyluracil I.1 is replaced by the phenyluracil I.65.

Preference is also given to the compositions 66.1-66.70 which differ from the corresponding compositions 1.1-1.70 only in that the phenyluracil I.1 is replaced by the phenyluracil I.66.

Preference is also given to the compositions 67.1-67.70 which differ from the corresponding compositions 1.1-1.70 only in that the phenyluracil I.1 is replaced by the phenyluracil I.67.

Preference is also given to the compositions 68.1-68.70 which differ from the corresponding compositions 1.1-1.70 only in that the phenyluracil I.1 is replaced by the phenyluracil I.68.

Preference is also given to the compositions 69.1-69.70 which differ from the corresponding compositions 1.1-1.70 only in that the phenyluracil I.1 is replaced by the phenyluracil I.69.

Preference is also given to the compositions 70.1-70.70 which differ from the corresponding compositions 1.1-1.70 only in that the phenyluracil I.1 is replaced by the phenyluracil I.70.

Preference is also given to the compositions 71.1-71.70 which differ from the corresponding compositions 1.1-1.70 only in that the phenyluracil I.1 is replaced by the phenyluracil I.71.

Preference is also given to the compositions 72.1-72.70 which differ from the corresponding compositions 1.1-1.70 only in that the phenyluracil I.1 is replaced by the phenyluracil I.72.

Preference is also given to the compositions 73.1-73.70 which differ from the corresponding compositions 1.1-1.70 only in that the phenyluracil I.1 is replaced by the phenyluracil I.73.

Preference is also given to the compositions 74.1-74.70 which differ from the corresponding compositions 1.1-1.70 only in that the phenyluracil I.1 is replaced by the phenyluracil I.74.

The weight ratios of the individual components in the compositions 1.1 to 74.70 are within the limits stated above, in the case of binary compositions of 3-phenyluracil I and 3-sulfonylisoxazoline II for example 1:1, 1:2 or 1:5, and in the case of ternary compositions of 3-phenyluracil I, 3-sulfonylisoxazoline II and safener III for example 1:1:1, 2:1:1, 1:2:1, 1:5:1 or 1:5:2.

In the ready-to-use preparations, i.e. in the compositions according to the invention in the form of crop protection products, the components I and II and optionally III, in suspended, emulsified or dissolved form, can be present formulated jointly or separately. The use forms depend entirely on the intended use.

The compositions according to the invention can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, broadcasting or watering. The use forms depend on the intended use; in any case, they should ensure the finest possible distribution of the active compounds.

Depending on the form in which the ready-to-use preparations are present in the compositions according to the invention, they comprise one or more liquid or solid carriers, if appropriate surfactants and if appropriate further auxiliaries which are customary for formulating crop protection products. The person skilled in the art is sufficiently familiar with the recipes for such formulations.

The ready-to-use preparations comprise the components I and II and optionally III and auxiliaries which are customary for formulating crop protection products, which auxiliaries may also comprise a liquid carrier.

Suitable inert additives with carrier function are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the active compounds I, II or III, as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignosulfite waste liquors or methylcellulose.

Powders, materials for spreading and dusts can be prepared by mixing or concomitant grinding of the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the active compounds in the ready-to-use preparations can be varied within wide ranges. In general, the formulations comprise from 0.001 to 98% by weight, preferably 0.01 to 95% by weight, of active ingredients. The active ingredients are employed in a purity of from 90% to 100%, preferably 95% to 100% (according to NMR spectrum).

The compounds according to the invention can, for example, be formulated as follows:

I 20 parts by weight of the active compound composition in question are dissolved in a composition composed of 80 parts by weight of alkylated benzene, 10 parts by weight of the adduct of 8 to 10 mol of ethylene oxide to 1 mol of oleic acid N-monoethanolamide, parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

II 20 parts by weight of the active compound composition in question are dissolved in a composition composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

III 20 parts by weight of the active compound composition in question are dissolved in a composition composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

IV 20 parts by weight of the active compound composition in question are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the composition is ground in a hammer mill. Finely distributing the composition in 20 000 parts by weight of water gives a spray composition which comprises 0.1% by weight of the active ingredient.

V 3 parts by weight of the active compound composition in question are mixed with 97 parts by weight of finely divided kaolin. This gives a dust which comprises 3% by weight of the active ingredient.

VI 20 parts by weight of the active compound composition in question are mixed intimately with 2 parts by weight of calcium dodecylbenzenesulfonate, 8 parts by weight of fatty alcohol polyglycol ether, 2 parts by weight of the sodium salt of a phenol-urea-formaldehyde condensate and 68 parts by weight of a paraffinic mineral oil. This gives a stable oily dispersion.

VII 1 part by weight of the active compound composition in question is dissolved in a composition composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the active compound composition in question is dissolved in a composition composed of 80 parts by weight of cyclohexanone and 20 parts by weight of Wettol® EM 31 (nonionic emulsifier based on ethoxylated castor oil). This gives a stable emulsion concentrate.

The components I and II and optionally III can be formulated jointly or separately.

The components I and II and optionally III can be applied jointly or separately, simultaneously or successively, before, during or after emergence of the plants.

If the active compounds I and II and optionally III are less well tolerated by certain crop plants, it is possible to use application methods in which the herbicidal compositions are sprayed with the aid of sprayers in such a way that the leaves of the sensitive crop plants are as far as possible unaffected, whereas the active compounds reach the leaves of the undesirable plants growing underneath or the uncovered soil surface (post-directed, lay-by).

The required application rate of the composition of the pure active compounds, i.e. of I and II and optionally III without formulation auxiliary, depends on the density of the undesired vegetation, on the development stage of the plants, on the climatic conditions of the location where the composition is used and on the application method. In general, the application rate of I and II and optionally III is from 0.001 to 3 kg/ha, preferably from 0.005 to 2 kg/ha and in particular from 0.01 to 1 kg/ha of active substance.

The required application rates of the 3-phenyluracils I and 3-sulfonylisoxazolines II are generally in the range from 0.1 g/ha to 1 kg/ha and preferably in the range from 1 g/ha to 500 g/ha or from 5 g/ha to 500 g/ha of active substance.

The compositions are applied to the plants mainly by spraying, in particular foliar spraying. Application can be carried out by customary spraying techniques using, for example, water as carrier and spray liquor rates of from about 100 to 1 000 l/ha (for example from 300 to 400 l/ha). Application of the herbicidal compositions by the low-volume and the ultra-low-volume method is possible, as is their application in the form of microgranules.

The compositions according to the present invention are suitable for controlling common harmful plants in useful plants, in particular in crops such as wheat, barley, oats, cereals, corn, soybean, sorghum, rice, oilseed rape, cotton, potatoes, dry beans, groundnuts, preferably crops of cereals, corn, soybeans, rice, oilseed rape, cotton, potatoes, groundnuts; more preferably cereals, corn, soybeans or rice; or in perennial crops. In another embodiment of the invention, they are useful for controlling the whole vegetation, i.e. they act as a total weedkiller. Furthermore, in another embodiment of the present invention, the compositions are useful for controlling undesirable vegetation in forestry.

Moreover, it may be useful to apply the compositions according to the invention jointly as a composition with other crop protection products, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

The compositions according to the invention can also be used in crop plants which are resistant to one or more herbicides owing to genetic engineering or breeding, which are resistant to one or more fungicides owing to genetic engineering or breeding, or which are resistant to attack by insects owing to genetic engineering or breeding. Suitable are for example crop plants, preferably corn, wheat, barley, sunflower, rice, canola, soybeans, which are resistant to herbicidal EPSP synthase inhibitors, such as, for example, glyphosate, to herbicidal glutamine synthase inhibitors, such as, for example, glufosinate, to herbicidal protoporphyrinogen-IX oxidase inhibitors, such as, for example, butafenacil, or to herbicidal ALS inhibitors, such as, for example, imazamethabenz, imazamox, imazapic, imazapyr, imazaquin, imazethapyr, or crop plants which, owing to introduction of the gene for Bt toxin by genetic modification, are resistant to attack by certain insects.

Surprisingly, the compositions according to the invention which comprise at least one 3-phenyluracil of formula I and at least one sulfonylisoxazoline of formula II have better herbicidal activity against harmful plants than would have been expected by the herbicidal activity of the individual compounds. In other words, the joint action of 3-phenyluracils of formula I and sulfonylisoxazolines of formula II results in an enhanced activity against harmful plants in the sense of a synergy effect (synergism). For this reason, the compositions can, based on the individual components, be used at lower application rates to achieve a herbicidal effect comparable to the individual components.

Surprisingly, the compositions according to the invention which, in addition to the 3-phenyluracil of formula I and the sulfonylisoxazoline of formula II, comprise a safener of formula III are better tolerated by useful plants than the respective composition of 3-phenyluracil I and sulfonylisoxazoline II without safener III.

The 3-phenyluracils of formula I can be prepared by the preparation processes disclosed by the earlier application WO 2001/83459. With respect to the preparation of individual compounds, reference is made to the examples of WO 2001/83459. Compounds which are not explicitly disclosed in this document can be prepared in an analogous manner.

The 3-sulfonylisoxazolines of formula II can be prepared by the preparation processes disclosed by the earlier applications JP 09/328,483, WO 01/12613, WO 02/62770, WO 03/00686, WO 03/10165, WO 04/13106, WO 04/14138 and JP 2005/35924. With respect to the preparation of individual compounds, reference is made to the examples of the quoted patent applications. Compounds which are not explicitly disclosed in this document can be prepared in an analogous manner.

USE EXAMPLES

The effect of the herbicidal compositions according to the invention of components I and II and, if appropriate, III on the growth of undesirable plants compared to the herbicidally active compounds alone was demonstrated by the following greenhouse experiments:

For the pre-emergence treatment, directly after sowing the active compounds, which had been suspended or emulsified in water, were applied by means of finely distributed nozzles. The containers were irrigated gently to promote germination and growth and subsequently covered with transparent plastic hoods until plant had rooted. This cover caused uniform germination of the tests plants, unless this was adversely affected by active compounds.

For the post-emergence treatment, the test plants were first grown to a height of 3 to 20 cm, depending on the plant habit, and only then treated. Here, the herbicidal compositions were suspended or emulsified in water as distribution medium and sprayed using finely distributing nozzles.

The respective components I and II and/or III were formulated as 10% by weight strength emulsion concentrate and introduced to the spray liquor with the amount of solvent system used for applying the active compound. In the examples, the solvent used was water.

The test period extended over 21 days. During this time, the plants were tended, and their response to the treatments with active compound was evaluated.

The evaluation for the damage caused by the chemical compositions was carried out using a scale from 0 to 100%, compared to the untreated control plants. Here, 0 means no damage and 100 means complete destruction of the plants.

The value E, which is to be expected if the activity of the individual compounds is just additive, was calculated using the method of S. R. Colby (1967) "Calculating synergistic and antagonistic responses of herbicide combinations", Weeds 15, p. 22 ff.

$$E=X+Y-(X\cdot Y/100)$$

where
- X=effect in percent using 3-phenyluracil I at an application rate a;
- Y=effect in percent using 3-sulfonylisoxazoline II at an application rate b;
- E=expected effect (in %) of I+II at application rates a+b.

If the value observed in this manner is higher than the value E calculated according to Colby, a synergistic effect is present.

The following compounds have been tested:
phenyluracil I.7 from table 1;
3-sulfonylisoxazoline II.1 from table 2.

The plants used in these greenhouse experiments belong to the following species:

| Scientific name | Common name |
| --- | --- |
| *Apera spica-venti* | windgrass |
| *Avena fatua* | wild oat |
| *Echinocloa crus-galli* | gulf cockspur |

Example 1

Herbicidal Activity of Composition 7.1 Applied by the Post-Emergence Method

| Application rate [g/ha] | | Herbicidal activity against *Apera spica-venti* | |
| --- | --- | --- | --- |
| I.7 | II.1 | found | caclulated |
| 4 | — | 15 | — |
| — | 62 | 10 | — |
| 4 | 62 | 50 | 23.5 |

Example 2

Herbicidal Activity of Composition 7.1 Applied by the Post-Emergence Method

| Application rate [g/ha] | | Herbicidal activity against *Avena fatua* | |
| --- | --- | --- | --- |
| I.7 | II.1 | found | caclulated |
| 4 | — | 20 | — |
| — | 62 | 10 | — |
| 4 | 62 | 35 | 28 |

Example 3

Herbicidal Activity of Composition 7.1 Applied by the Post-Emergence Method

| Application rate [g/ha] | | Herbicidal activity against *Echinocloa crus-galli* | |
| --- | --- | --- | --- |
| I.7 | II.1 | found | caclulated |
| 2 | — | 50 | — |
| — | 31 | 55 | — |
| 2 | 31 | 90 | 77.5 |

The data according to examples 1 to 3 prove unambiguously the synergistic effect of the herbicidal mixtures according to the invention.

We claim:

1. A herbicidal composition comprising a synergistic combination of
    a) at least one 3-phenyluracil I of formula I

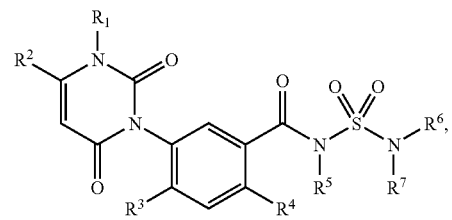

wherein the variables $R^1$ to $R^7$ are as defined below:
$R^1$ is methyl;
$R^2$ is $C_1$-$C_2$-haloalkyl;
$R^3$ is halogen;
$R^4$ is halogen;
$R^5$ is hydrogen;
$R^6$, $R^7$ independently of one another are $C_1$-$C_6$-alkyl;
or an agriculturally acceptable salt thereof; and
    b) at least one 3-sulfonylisoxazoline II of formula II

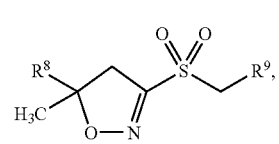

wherein the variables $R^8$ and $R^9$ are as defined below:
$R^8$ is $C_1$-$C_4$-alkyl;
$R^9$ is phenyl or pyrazolyl,
    wherein each of the aforementioned heterocycles may be unsubstituted or substituted by 1 to 3 substituents selected from the group consisting of halogen, $C_1$-$C_6$-alkyl, $C_1$-$C_4$-haloalkyl, and $C_1$-$C_4$-haloalkoxy.

2. A herbicidal composition as claimed in claim 1 wherein the variables $R^1$ to $R^7$ in formula I are as defined below:
$R^1$ is methyl;
$R^2$ is trifluoromethyl;
$R^3$ is fluorine or chlorine;
$R^4$ is halogen;
$R^5$ is hydrogen;

$R^6$ is $C_1$-$C_6$-alkyl
$R^7$ is isopropyl.

3. A herbicidal composition as claimed in claim 1, wherein $R^6$ and $R^7$ in formula I are identical or different $C_1$-$C_6$-alkyl radicals.

4. A herbicidal composition as claimed in claim 1, wherein $R^9$ in formula II is 4-pyrazolyl, which may be unsubstituted or substituted by 1 to 3 halogen atoms and/or 1, 2 or 3 substituents selected from the group consisting of $C_1$-$C_6$-alkyl, $C_1$-$C_4$-haloalkyl, and $C_1$-$C_4$-haloalkoxy.

5. A herbicidal composition as claimed in claim 1, wherein in formula II
$R^8$ is methyl; and
$R^9$ is 4-pyrazolyl,
which may be unsubstituted or substituted by 1 to 3 halogen atoms and/or by 1 to 3 substituents selected from the group consisting of $C_1$-$C_4$-alkyl, $C_1$-$C_4$-haloalkyl, and $C_1$-$C_4$-haloalkoxy.

6. A herbicidal composition as claimed in claim 1, wherein the variables $R^8$ and $R^9$ in formula II are as defined below:
$R^8$ is methyl;
$R^9$ is 4-pyrazolyl,
which may be unsubstituted or substituted by 1 to 3 halogen atoms and/or by 1 or 2 substituents selected from the group consisting of $C_1$-$C_4$-alkyl, $C_1$-$C_4$-haloalkyl, and $C_1$-$C_4$-haloalkoxy.

7. A herbicidal agent comprising the herbicidal composition as claimed in claim 1, further comprising at least one inert liquid and/or solid carrier, and, optionally, at least one surfactant and, optionally at least one further auxiliaries.

8. A method for controlling undesirable vegetation, which comprises applying a herbicidally effective amount of a herbicidal composition as claimed in claim 1 to act on the undesirable vegetation, their habitat or on seed.

9. A method for controlling undesired vegetation as claimed in claim 8, which comprises applying the herbicidal composition before, during and/or after the emergence of the undesirable plants to the undesirable vegetation, their habitat or on seed; the components I and II being applied simultaneously or in succession.

10. The method as claimed in claim 9 wherein the undesirable vegetation is in crops which are crops of wheat, barley, oats, cereals, corn, soybean, sorghum, rice, oilseed rape, cotton, potatoes, dry beans or groundnuts.

11. The method as claimed in claim 9 for controlling undesirable vegetation in crops which are selected from the group consisting of cereals, rice, soybeans and corn.

12. The method as claimed in claim 9, wherein the method controls undesirable vegetation in forestry.

13. The method as claimed in claim 9, wherein the method controls undesirable vegetation in crop plants, where the crop plants are resistant to one or more herbicides due to genetic engineering and/or breeding.

14. The method of claim 9, wherein the herbicidal composition is applied at a rate of 0.001 to 3 kg/ha of active substances.

15. The method of claim 14, wherein the herbicidal composition is applied at a rate of 0.005 to 2 kg/ha of active substances.

16. The method of claim 15, wherein the herbicidal composition is applied at a rate of 0.01 to 1 kg/ha of active substances.

17. The method of claim 14, wherein the phenyluracil(s) I and the sulfonylisoxazoline(s) II are each applied at a rate of 0.1 g/ha to 1 kg/ha.

18. The method of claim 17, wherein the phenyluracil(s) I and the sulfonylisoxazoline(s) II are each applied at a rate of 1 g/ha to 500 g/ha.

* * * * *